United States Patent [19]
Strobel

[11] 3,937,808
[45] Feb. 10, 1976

[54] SUN TANNING AND HARI PROTECTING ACID SALTS OF AMINOMETHYL-O-HYDROXYPHENONES COMPOSITIONS

[75] Inventor: Albert F. Strobel, Delmar, N.Y.

[73] Assignee: GAF Corporation, New York, N.Y.

[22] Filed: Dec. 17, 1973

[21] Appl. No.: 425,693

Related U.S. Application Data

[63] Continuation-in-part of Ser. No. 230,458, Feb. 29, 1972, abandoned.

[52] U.S. Cl............ 424/59; 260/45.9 R; 260/570.9; 424/70; 424/301; 424/317; 424/330
[51] Int. Cl.²...................... A61K 7/06; A61K 7/42; A61K 31/12; A61L 13/00
[58] Field of Search ....... 424/59, 70, 301, 317, 330; 260/45.9, 294.7, 570.9, 293.8

[56] References Cited
UNITED STATES PATENTS

| | | | |
|---|---|---|---|
| 2,763,657 | 9/1956 | Allen | 260/294.7 |
| 3,058,886 | 10/1962 | Kreps | 424/59 |
| 3,380,961 | 4/1968 | Dressler | 260/45.9 |

Primary Examiner—Sam Rosen
Assistant Examiner—A. P. Fagelsan
Attorney, Agent, or Firm—Walter C. Kehm

[57] ABSTRACT

A novel class of acid addition salts of aminomethyl-o-hydroxyphenones having ultraviolet absorbing properties in the 300–350 mu range having the following formula:

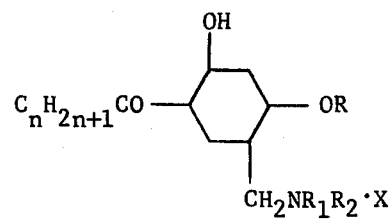

wherein R represents hydrogen or an alkyl radical of from 1 to 4 carbon atoms, $R_1$ and $R_2$ each represents an alkyl radical of from 1 to 4 carbon atoms, n has a value of 1 to 3 and X is an acid moiety selected from the group of hydrochloric, hydrobromic, sulfuric, phosphoric, acetic, formic, propionic, p-toluene sulfonic, behenic, benzene sulfonic, tartaric, citric and benzoic acids. These salts have been found to be skin substantive and particularly adapted for use as sunscreening and/or sun-tanning agents.

9 Claims, No Drawings

SUN TANNING AND HAIR PROTECTING ACID SALTS OF AMINOMETHYL-O-HYDROXYPHENONES COMPOSITIONS

This application is a continuation-in-part of U.S. application Ser. No. 230,458, filed Feb. 29, 1972, now abandoned, and incorporates herein the disclosure of the parent application.

This invention relates to a novel class of acid salts of aminomethyl-o-hydroxyphenones which have useful ultraviolet absorbing properties. More particularly, this invention relates to addition salts of aminomethyl-o-hydroxyphenones having ultraviolet absorbing properties in the 300–350 m$\mu$ range peaking between 300 and 325 m$\mu$ and to methods of making and using the same.

Various organic compounds are known to possess the ability to absorb electromagnetic radiations within the band of 2,900 to 3,700 A. When such compounds are incorporated into various plastic materials such as, for instance, transparent plastic sheets and foils, the resultant products act as filters for all of the radiation passing therethrough transmitting only such radiations as are not absorbed by the sheet and/or absorbing agent. It is thereby made possible to screen out undesirable radiations and to utilize such transparent plastic sheet and foil materials as a filter in connection with a large number of applications including, for example, as wrappings for food products and the like. While a large number of organic compounds have already been proposed for use as absorbents for radiations in the above-noted range, their incorporation into plastic sheet and foil materials and their use has been limited to the purposes noted above.

It is known that a great concern exists with respect to ultraviolet radiations emanating from the sun. The sun-derived radiations which are known to have deleterious effects are those having wavelengths of between about 250 m$\mu$ and 400 m$\mu$. The effects of radiation on the human skin is a subject of highly specialized study wherein skin sensitivity and substantivity as well as absorbability resulting for instance from suntan and sunburn of harmful wavelengths must be taken into consideration for composition proposed as a suntanning agent. The rays of the sun which cause burning of the skin are those whose wavelengths are between 295 and 320 m$\mu$, whereas those which cause tanning have wavelengths between 325 and 370 m$\mu$.

Other effects of ultraviolet radiation which are also of considerable importance relate to the photochemical degradation of many products which are either unstable following exposure to such radiation or are affected to the extent that they are no longer useful or, for that matter, salable. Many plastic materials when exposed to ultraviolet radiation within the range of 250 to 400 m$\mu$, and particularly 325 to 400 m$\mu$, undergo degradation resulting in the substantial development of undesirable color bodies with a subsequent loss in transparency of the plastic. Food products, in addition to becoming discolored, often are, following such exposure, unfit for human consumption. Thus, for instance, following prolonged exposure to ultraviolet light, fruits, edible oils, butter and other food products tend to spoil and turn rancid. Further, it is well known that colored articles such as dyed textiles fade following exposure to sunlight and, in particular, to ultraviolet light. Many plastic materials in addition to developing undesirable color resulting in the reduction of transparency also become brittle, lose their elasticity, crack and eventually completely deteriorate. Paints, varnishes, lacquers and the like are particularly prone to these effects, although in connection with these latter materials, the transparency factor may be of paramount concern.

Accordingly, it is an object of this invention to provide a relatively inexpensive composition which displays optimum absorption activity for ultraviolet radiations within the range of 320 to 400 m$\mu$.

Another object of the invention is to provide a method for making such ultraviolet radiation absorbent compositions.

Still another object of the invention is to provide ultraviolet absorbing compositions containing a new compound.

Yet a further object of the invention is to provide compositions particularly adapted for use as sun-tanning and/or sun-screening agents containing the compounds of the invention.

Other objects and advantages of the present invention will become apparent from consideration of the following description.

The new compounds of the invention can be represented by the formula:

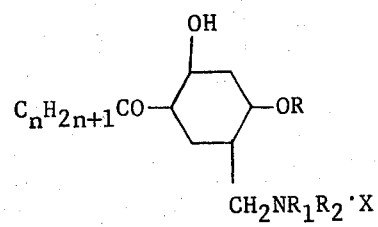

wherein R represents hydrogen or lower alkyl such as methyl, ethyl, propyl, isopropyl, butyl, isobutyl and tert. butyl, $R_1$ and $R_2$ each represents an alkyl group such as methyl, ethyl, propyl, isopropyl, butyl, isobutyl and tert. butyl, n has a value of 1 to 3 and X is an acid selected from the group of acids including hydrochloric, hydrobromic, sulfuric, phosphoric, acetic, formic, propionic, p-toluene sulfonic, behenic, citric, benzene sulfonic, tartaric and benzoic acids. The compounds of the invention are, thus, the acid addition salts of aminomethyl-o-hydroxyphenones.

Phenyl substituents in the above composition are excluded since compounds in this group absorb ultraviolet light beyond the wavelength useful for the purposes of preventing burning of the skin. For example, the chloride salt of 254-dihydroxyphenylphenone shows absorption activity in the 330–350 m$\mu$ range and peak activity about 338–340 m$\mu$, which is beyond the wavelengths which cause sun burning but which fall within those which provide desirable sun tanning.

According to the invention, the compounds of the above formulae are prepared by reacting a compound having the following formula:

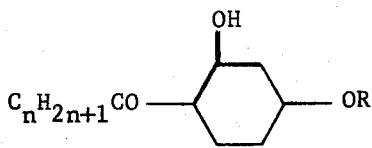

wherein R has the same meaning as set out above with formaldehyde and a secondary amine having the formula:

wherein $R_1$ and $R_2$ are each as above defined, at a temperature between about 50° and about 100°C. under a pressure of from atmospheric to about 200 psig. in an aqueous medium to provide the corresponding aminomethyl-o-hydroxyphenone and then reacting this intermediate product with an acid selected from the above group to form the acid addition salt thereof. Preferably the reaction to form the aminomethyl-o-hydroxyphenone is effected under reflux conditions in the presence of an inert diluent and most preferably in the presence of an alcohol such as ethanol, isopropanol, methanol and the like. Generally, the acid is added after removing the diluent and, in cases where the reaction mixture is at a temperature above 80°C., after the intermediate product mixture is cooled to a temperature between about 50° and about 75°C.

Heat has been found to accelerate the reaction to form the phenone, although temperatures varying from room temperature to the reflux temperature of the reaction mixture at whatever pressure is applied can be employed. The formaldehyde can be employed in the form of its highly concentrated aqueous solution or as paraformaldehyde.

Examples of particularly useful secondary amine reactants are dimethylamine, methylethylamine, diethylamine, dipropylamine, diisobutylamine, di-n-butylamine, and diisopropylamine. Other secondary amines which can be employed include di-t-butylamine, ethylpropylamine, n-butylethylamine and others.

In the resulting aminomethylhydroxyphenone intermediates of the present invention, it is necessary that the amine grouping be a tertiary amine group having strongly basic properties so that it will readily react with the acid to form a stable salt. Since secondary amines are weakly basic, their addition salt derivatives are comparatively unstable and, thus, the secondary amine group is excluded from the products of the present process.

The novel acid addition salts of the invention are characterized in that they display high absorption activity for radiations in the 300–350 m$\mu$ range and reach peak absorption within the range of 310 to 330 m$\mu$. It is thus seen that they absorb most of the radiation producing burning of the skin and some radiation producing tanning while transmitting some radiation in the tanning range. The tanning as compared to the sunscreening effect is dependent on the thickness of the film containing the active component as well as on the concentration of the active component in such film. For example, a 2% or less solution of the active agent will allow tanning and substantially no burning while a 10% solution acts as a total sunscreen blocking out both tanning and burning rays.

The compounds of the invention are also characterized by their excellent substantivity to proteinaceous material such as skin and hair. As a result, they have the considerable advantage in that they are resistant to removal by water. This represents an improvement over the presently available commercial sun-tan agents such as glyceryl p-aminobenzoate and 2-hydroxy-4-methoxy-5-benzophenonesulfonic acid as these compounds are not substantive to skin and hair and are, therefore, easily washed off on contact with water.

Suitable carriers for the acid salts of this invention include water and aqueous solutions of methanol, ethanol, glycerol, isopropanol, emulsions in vegetable oil or mineral oil, water being preferred in concentrations between about 60 and 100 percent of the carrier solution. The salt is generally employed in the solution in concentrations between about 0.05 and about 25% of the total solution. For applications to the skin or hair, a salt concentration of between about 0.4 and 10% is preferred.

The present acid addition salts may also be employed for other applications such as ingredients in plastic compositions to prevent their degradation under extended exposure to ultraviolet light and to prevent deterioration of edible products packaged in such plastic material. Being water soluble and highly stable, the present compounds are easily incorporated during the manufacture of the plastic and thus display important advantages over compounds containing zwitterion structure which are substantially insoluble in water and which, being weak bases, form less stable salts.

The following examples will serve to illustrate the invention but are nowise to be construed as limiting the scope thereby.

EXAMPLE 1

Preparation of the compound having the formula:

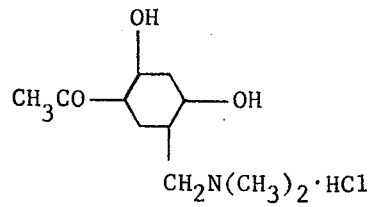

27 G. Resacetophenone, 39 g. dimethylamine (40% aqueous), 23 g. water, 18 g. formaldehyde (37% aqueous) and 125 g. ethanol were refluxed for four hours at 83°C. Thereafter, the excess ethanol and dimethylamine were distilled off. 18 cc. concentrated hydrochloric acid (38% aqueous) were added to the resultant reaction mixture until Congo Blue acidity had been reached. The reaction mixture was then evaporated to dryness on a steam bath forming a tacky solid.

A 5% solution of the compound as set out in the above formula in water was applied to the skin of a number of subjects and allowed to air dry thereon. Thereafter, the skin was exposed to ultraviolet light. The skin in the area to which the solution had been applied was protected whereas the skin which had not been covered with the solution showed evidence of burning.

The protection afforded by a solution of glyceryl p-aminobenzoate and a solution of a product of the example to skin following washing with water was determined by applying solutions of each of the compounds to different areas of skin, allowing the same to dry thereon and then washing the areas with water. It was found that while the product of this example afforded protection on exposure of the skin to ultraviolet light, burn areas developed at the sites where the glyceryl p-aminobenzoate had been applied. The foregoing results demonstrate the substantivity of this product in contrast to the non-substantivity of the commercial glyceryl p-aminobenzoate.

EXAMPLE 2

Preparation of a compound having the formula:

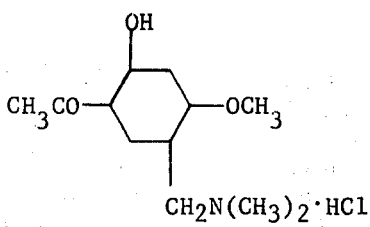

83 G. 2-hydroxy-4-methoxyacetophenone (0.5 mole), 155 g. dimethylamine (40% aqueous), 93 g. water, 75 g. formaldehyde (37% aqueous) and 500 g. ethanol were mixed together and the resultant mixture heated under reflux at 83°C. for 12 hours. The ethanol and dimethylamine still present were then distilled off and the mixture cooled to room temperature. 70 Ml. concentrated hydrochloric acid (38% aqueous) was added until Congo Blue acidity was reached. The reaction mixture was then evaporated on a steam bath forming a tacky solid.

When the product of this example was applied to the skin as described for the novel addition salt in Example 1, similar results were obtained.

EXAMPLE 3

Preparation of a compound having the formula:

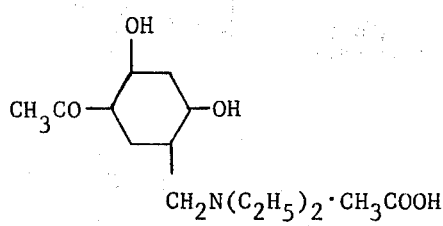

The procedure as set out in Example 1 was followed with the exception that the dimethylamine was replaced by an equivalent amount of diethylamine. Following completion of the reaction, the alcohol and diethylamine were distilled off and an equimolar amount of acetic acid was used in place of the hydrochloric acid of Example 1. The reaction mixture was evaporated on a steam bath forming a tarry solid.

When this compound was applied to the skin by the procedure disclosed for the acid addition salt in Example 1, substantially the same results were obtained.

Hair was immersed in a 5% solution of the compound of the example. The excess material was squeezed out and the hair dried. The hair so treated was more resistant to light fading than hair which had been subjected to similar treatment but in the absence of the effective compound of the example.

Hair which had been subjected to dyeing was thereafter treated with a solution of the compound of this example. Following exposure to ultraviolet light, the hair maintained its color without change. Untreated, dyed hair, when subjected to ultraviolet light exposure underwent a noticeable change in color.

EXAMPLE 4

A hair shampoo having the following composition was prepared in the conventional manner:

| | |
|---|---|
| Lauric monoglyceride sodium sulfate | 20.00% |
| Behenic acid | 3.00% |
| Triethanolamine | 3.00% |
| Citric acid | 0.70% |
| Perfume | 0.40% |
| Water | 72.75% |

There was then added to the resultant shampoo sufficient compound of Example 1 to provide a concentration of 0.5% in the formulation. A further batch of shampoo was similarly prepared but using, instead of the compound of Example 1, the compound of Example 3. After shampooing with the formulations thusly prepared, the hair was exposed to ultraviolet radiation. No discoloration or embrittlement was observed in any instance. When the procedure was repeated using subjects with dyed hair, substantially the same results were obtained.

The aminomethyl-o-hydroxyphenones of the invention are also useful as filters for ultraviolet radiation in plastics in place of the ultraviolet absorbing agents heretofore available. In addition, they may be used in the preparation of filter layers for photographic elements, such as color photographs on opaque supports which are susceptible to image degradation on exposure to ultraviolet radiation. Such filter elements prepared with the compounds of the invention evidence high absorption of radiation between the wavelengths 310–350 m$\mu$ and this absorption does not diminish even after prolonged exposure.

EXAMPLE 5

Preparation of a compound having the formula:

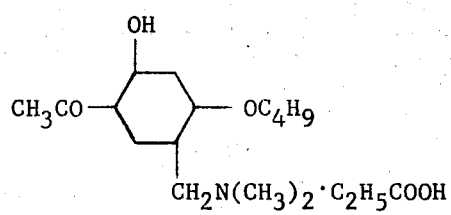

96 G. 2-hydroxy-4-butoxyacetophenone (0.5 mole), 155 g. dimethylamine (40% aqueous), 93 g. water, 75 g. formaldehyde (37% aqueous) and 500 g. propanol are mixed together and the resultant mixture heated under reflux conditions for 12 hours. The propanol and dimethylamine remaining after reaction are then distilled off and the mixture cooled to 60°C. temperature. 70 ml. propionic acid is added until a pH of 3.5 is reached. The mixture is then evaporated on a steam bath until a soft solid is formed. When the product of this example is applied to the skin as described for the novel addition salt in Example 1, no burning occurs where the compound is applied.

EXAMPLE 6

Preparation of a compound having the formula:

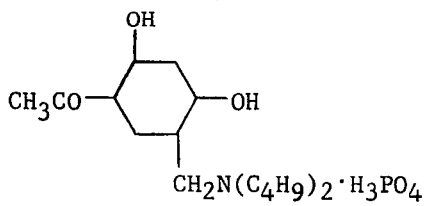

The procedure as set out in Example 1 is followed with the exception that the dimethylamine is replaced by an equivalent amount of di-t-butylamine. Following completion of the reaction, the alcohol and ditertiary butylamine are distilled off and an equal molar amount of phosphoric acid is used in place of the hydrochloric acid of Example 1 until a pH of 3 is obtained. The reaction mixture is evaporated on a steam bath forming a soft solid. When this compound is applied to the skin by the procedure for the addition salt in Example 1, substantially no burning occurs where the compound is applied.

EXAMPLE 7

The preparation of a compound having the formula:

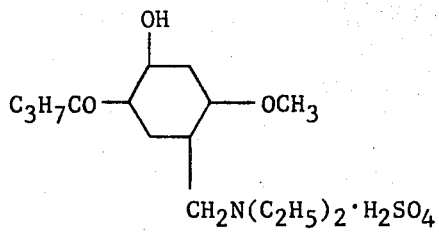

The procedure as set out in Example 2 is followed with the exception that 2-hydroxy-4-methoxyacetophenone is replaced with 2-hydroxy-4-methoxybutyrophenone and dimethylamine is replaced with diethylamine in equivalent amounts. Following the completion of the reaction, the alcohol and diethylamine are distilled off and an equal molar amount of sulfuric acid is used in place of the hydrochloric acid of Example 1. The reaction mixture is evaporated on a steam bath forming a solid product. When this compound is applied to the skin by the procedure disclosed for the addition salt in Example 1, substantially no burning occurs in the areas where the compound is applied.

EXAMPLE 8

The preparation of a compound having the formula:

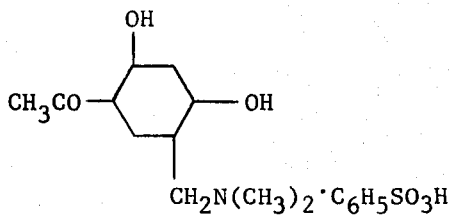

The procedure as set out in Example 1 is repeated except that benzensulfonic acid is substituted for hydrochloric acid. When this compound is applied to the skin by the procedure disclosed for the addition salt in Example 1, substantially no burning occurs where this compound is applied.

What is claimed is:

1. A sun tanning and hair protecting composition comprising between about 0.4% and about 10% by weight of a compound selected from the group consisting of acid addition salts of a compound having the formula:

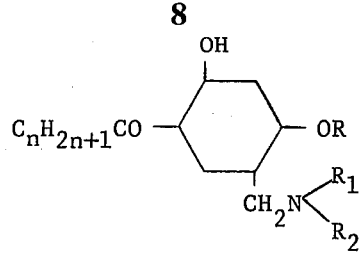

wherein R is hydrogen or an alkyl having from 1–4 carbon atoms, $R_1$ and $R_2$ each represents an alkyl having from 1–4 carbon atoms and $n$ has a value of 1 to 3, said compound having ultra-violet absorption in the sun burning range of 300–350 m$\mu$ while transmitting radiation in the sun tanning range; and a carrier selected from the group consisting of water, vegetable oil, mineral oil, and aqueous solutions of methanol, ethanol, glycerol and isopropanol.

2. The composition of claim 1 wherein the acid of the addition salt is selected from the group consisting of hydrochloric acid, acetic acid, hydrobromic acid, sulfuric acid, phosphonic acid, formic acid, propionic acid, p-toluene sulfonic acid, benzene sulfonic acid, behenic acid, citric acid, benzoic acid, and tartaric acid.

3. The composition of claim 1 wherein said compound has the formula:

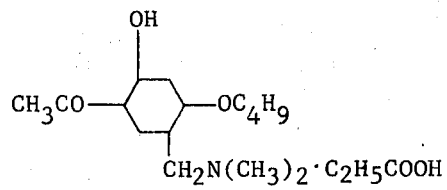

4. The composition of claim 1 wherein said compound has the formula:

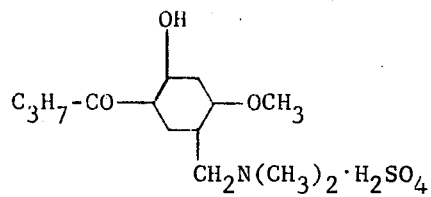

5. The composition of claim 1 wherein said compound has the formula:

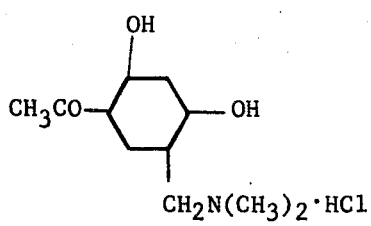

6. The composition of claim 1 wherein said compound has the formula:

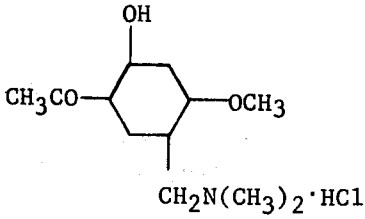

7. The composition of claim 1 wherein said compound has the formula:

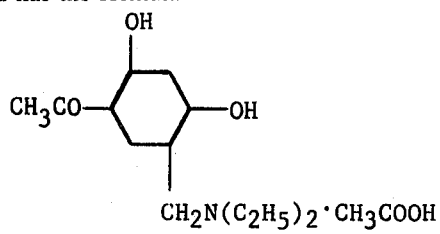

8. Method of protecting hair against discoloration on exposure to ultraviolet radiation comprising applying to the hair an effective amount of the composition of claim 1 prior to such exposure.

9. Method of protecting skin against undue tanning or burning on exposure of the skin to ultraviolet radiation which comprises applying to the skin an effective amount of the composition of claim 1 prior to such exposure.

* * * * *